United States Patent [19]

Reising et al.

[11] Patent Number: 4,681,580
[45] Date of Patent: Jul. 21, 1987

[54] DISPOSABLE DIAPERS WITH UNITARY WAISTSHIELD AND ELASTICALLY EXPANSIBLE WAISTBANDS

[75] Inventors: George S. Reising, Batavia; Jerry L. Dragoo, Cincinnati, both of Ohio

[73] Assignee: The Procter & Gamble Company, Cincinnati, Ohio

[21] Appl. No.: 717,749

[22] Filed: Mar. 29, 1985

[51] Int. Cl.[4] ............................................. A61F 13/16
[52] U.S. Cl. ............................................. 604/385 A
[58] Field of Search .................. 604/358, 385 A, 386, 604/379, 380, 382, 396, 385.2

[56] References Cited

U.S. PATENT DOCUMENTS

| 4,090,515 | 5/1978 | Karami | 604/382 |
| 4,397,645 | 8/1983 | Buell | 604/380 |
| 4,450,026 | 5/1984 | Pienak et al. | 604/385 A |
| 4,486,192 | 12/1984 | Sigl | 604/382 |
| 4,515,595 | 5/1985 | Kievet et al. | 604/385 A |
| 4,578,071 | 3/1986 | Buell | 604/379 |

*Primary Examiner*—John D. Yasko
*Attorney, Agent, or Firm*—John M. Pollaro; Fredrick H. Braun; Richard C. Witte

[57] ABSTRACT

Disposable diapers having liquid impermeable waistshields and elastically expansible waistbands. The waistshields and waistbands are formed of a single—unitary—liquid impermeable material. In preferred embodiments, the waistshield/waistband is formed of a material which has a heat unstable state and a heat stable and elastic state. In diapers ready for use, the waistband portion is relatively more heat stable and elastic than the waistshield portion.

6 Claims, 4 Drawing Figures ial No. 06/444,543, filed Nov. 26, 1983, describe disposable diapers with elastically expansible waistbands.

DISPOSABLE DIAPERS WITH UNITARY WAISTSHIELD AND ELASTICALLY EXPANSIBLE WAISTBANDS

BACKGROUND OF THE INVENTION

1. Field of the Invention

This invention concerns disposable diapers, incontinent briefs, and the like having at least one unitary waistshield and elastically expansible waistband.

2. Background Art

Infants (and other incontinents) wear disposable diapers to receive and contain urine, feces, and other fluids discharged from the body. Disposable diapers function both to contain the discharged materials and to isolate these materials from the body of the wearer and from the wearer's surroundings. Modern embodiments of disposable diapers frequently perform these tasks in a manner superior to that of traditional cloth diapers.

Disposable diapers normally comprise three elements: a fluid permeable topsheet designed to be placed next to the wearer's skin; a liquid impermeable backsheet which forms, in use, the outer surface of the diaper; and an absorbent element interposed between the topsheet and the backsheet.

The topsheet is frequently a hydrophobic non-woven fabric which is readily permeable to fluid. Its hydrophobicity tends to cause the surface in contact with the wearer's skin to be dry and protected from fluids absorbed within the absorbent element.

The absorbent element receives and retains fluids which pass through the topsheet. It normally comprises a batt of airlaid wood pulp fibers.

The backsheet functions to contain fluids within the absorbent element thereby protecting the wearer's outer garments and other surfaces from soiling by these fluids. Backsheets are commonly formed of liquid impermeable material such as polyethylene film.

Disposable diapers having many different basic designs are known to the art. For example, Duncan and Baker in U.S. Pat. No. Re. 26,152, issued Jan. 31, 1967, described and claim a disposable diaper which has achieved wide acceptance and commercial success. Buell, in U.S. Pat. No. 3,860,003, issued Jan. 14, 1975, described and claims another disposable diaper which, too, has achieved wide acceptance and commercial success. The diaper taught by Buell differs from that taught by Duncan and Baker in many respects, not the least of which is the provision in the Buell diaper of elasticized (or expansible) leg cuffs. Another embodiment of disposable diapers is described and claimed by Aziz and Blaney in European Patent Application No. 82200801.7, filed June 29, 1982. The Aziz and Blaney diaper also provides elasticized (or expansible) leg cuffs, but is of a somewhat different design than that described by Buell.

Mesek et al in U.S. Pat. No. 4,324,245, issued Apr. 13, 1982; Pieniak et al in U.S. Pat. No. 4,337,771, issued July 6, 1982; and Mesek et al in U.S. Pat. No. 4,352,355, issued Oct. 5, 1982 describe disposable diapers having elasticized cuffs and elasticized (or expansible) waistbands.

Kievit and Osterhage, in European Patent Application No. 83307177.2, published June 4, 1984 as publication No. 0112655, based on U.S. Patent Application Ser. No. 06/444,543, filed Nov. 26, 1983, describe disposable diapers with elastically expansible waistbands.

Buell, in European Patent Application No. 82200161.6, published Sept. 1, 1982 as publication No. 0059015, describes disposable diapers with waistshields. A waistshield is a liquid impermeable barrier member provided at the edge of the absorbent core in at least one of the waist regions of the diaper. It comprises an outward portion projecting from the edge of the absorbent core away from the center of the diaper and an inward portion interposed between the topsheet and the absorbent core. The waistshield serves to prevent liquid from escaping from the absorbent core through its waist edges.

Other concepts have also been proposed to prevent the liquid which migrates toward the perimeter of the diaper from wetting the wearer's undergarments. For example, U.S. Pat. No. 3,520,303 which issued to Endres on July 14, 1970, teaches a disposable diaper having a leak-preventing barrier at the ends to prevent leakage at the waist. The barrier is a strip of thin film which is affixed between the topsheet and the backsheet along a single line at the perimeter of the diaper. Endres et al., in U.S. Pat. No. 3,900,031 issued Aug. 19, 1975, also disclose a thin film at the edge of a diaper.

Strickland and Visscher in U.S. Pat. No. 4,253,461, issued on Mar. 3, 1981, describe and claim another form of disposable diaper sometimes referred to as an incontinent brief and intended to be worn by adults.

While the disposable diapers described above, particularly those described by Duncan and Baker, Buell, and Aziz and Blaney, and Kievit and Osterhage, function in an exemplary manner, improved disposable diapers are still sought.

SUMMARY OF THE INVENTION

The present invention is of a disposable diaper comprising a unitary waistband and elastically expansible waistband. In this invention, a single (unitary) piece of material serves as a waistshield (liquid impermeable barrier) which prevents liquid form escaping from the absorbent core through its waist edges thereby rendering the body-contacting surface of the diaper dryer, and as an elastically expansible waistband which enhances the fit of the diaper about the wearer's waist and which tends to retard leakage of fluid from the waist area.

DETAILED DESCRIPTION OF THE INVENTION

Referring now to figures, there is shown one preferred embodiment of the present invention as it would be used in a disposable absorbent article and, more particularly, as it would be used in a disposable diaper. As used herein, the term "disposable absorbent article" refers to articles which absorb and contain liquid, and, more specifically, refers to articles which are placed adjacent the human body to absorb and contain the various bodily discharges (e.g., blood, menses, urine, etc.), which articles are intended to be discarded after a single use rather than being laundered or otherwise restored and reused. A "diaper" is a garment generally worn by infants and incontinent persons; it is placed between the legs and fastened about the waist of the wearer (user). It should be understood, however, that while the present invention is discussed in terms of a diaper, it is also applicable for use in other disposable absorbent articles such as catamenial pads, briefs and the like.

Figure 1:
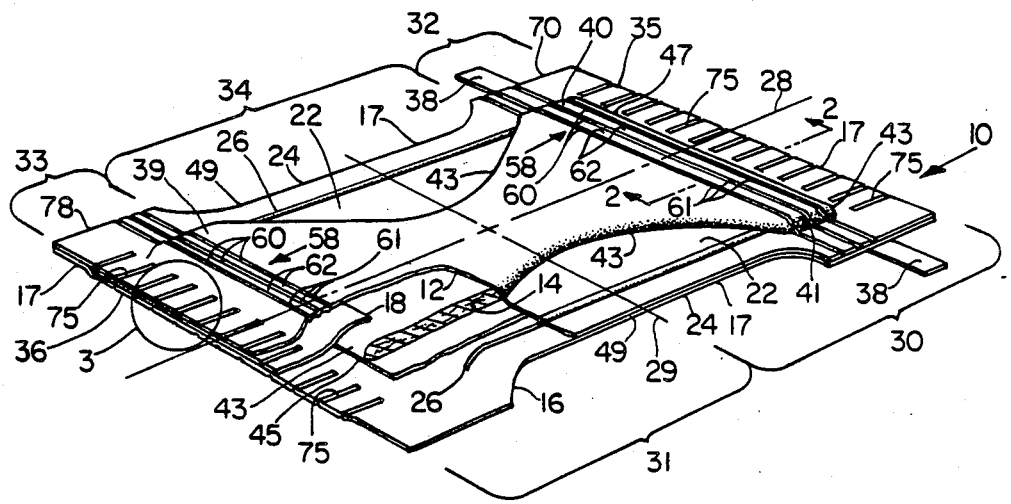
FIG. 1 is a partially cutaway perspective view of a disposable diaper incorporating the present invention; the thicknesses of certain elements have been exaggerated for clarity.

FIG. 1 is a partially cut-away plan view of a preferred disposable diaper 10 of the present invention after the elements are assembled, but before the unitary waistshield and elastically expansible waistband member (hereinafter for simplicity referred to as "waistshield/waistband") is contracted as described infra, and diaper 10 before it is placed on the diaper user. As seen in FIG. 1, diaper 10 basically comprises a fluid permeable topsheet 12, an absorbent core 14, a liquid impermeable backsheet 16, and waistshield/waistband 18. While topsheet 12, absorbent core 14, and backsheet 16 may be assembled in a variety of well known configurations, a preferred disposable diaper assembly is described generally in the aforementioned U.S. Pat. No. 3,860,003 issued to Buell, which patent is incorporated herein by reference.

Figure 2:
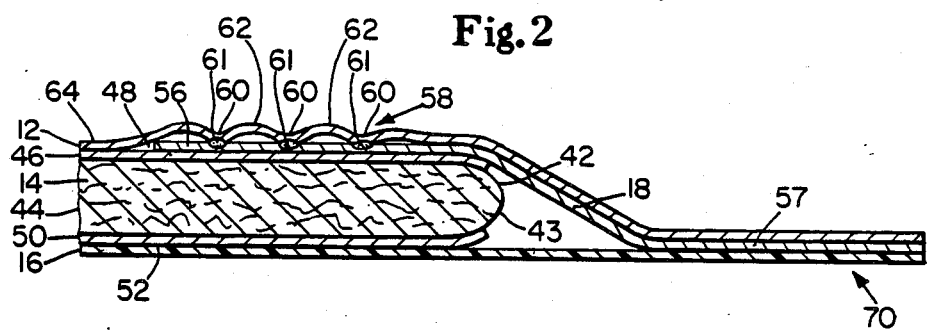
FIG. 2 is a cross-sectional view of the diaper of FIG. 1 taken along line 2—2; the thicknesses of certain elements have been exaggerated for clarity.

In the preferred embodiment of diaper 10 shown in FIGS. 1 and 2, in which topsheet 12 and backsheet 16 are coextensive and have length and width dimensions generally larger than those of absorbent core 14. Topsheet 12 is superposed on backsheet 16 thereby forming a peripheral edge 17. Peripheral edge 17 defines the outer periphery or the outer extent of diaper 10 and encircles absorbent core 14. Topsheet 12 is affixed to backsheet 16 in any suitable manner known in the art by means generally not shown in the figures except in connection with other functions.

Diaper 10 has a side flap 22 on each longitudinal side 24 of diaper 10. For the purpose of providing an elasticized expansible line within side flap 22, an elastic member 26 is associated with each side flap 22 thereby providing an elastically expansible edge 49 in each side flap 22. More detailed and specific information concerning side flaps 22 and elastic member 26 is set forth in the hereinabove incorporated U.S. Pat. No. 3,860,003.

Disposable diaper 10 has a longitudinal centerline 28, a lateral centerline 29, a rear portion 30, a front portion 31, a rear waist portion 32, a front waist portion 33, and a crotch portion 34. Further, peripheral edge 17 comprises rear edge 35 and front edge 36 each extending the distance between longitudinal sides 24 at either end of disposable diaper 10.

Rear portion 30, in general, is that part of the diaper from laterial centerline 29 to rear edge 35 of diaper 10 and which, when diaper 10 is worn, contacts the back of the infant. Front portion 31, in general, is that portion of diaper 10 form lateral centerline 29 to front edge 36 of diaper 10 and which, when diaper 10 is worn contacts the front of the infant. Rear waist portion 32 is that marginal portion of diaper 10 adjacent rear edge 35. Front waist portion 33 is that marginal portion of diaper 10 adjacent front edge 36. Rear and front waist portions 32 and 33, respectively, cooperate with each other when diaper 10 is fitted about and attached to an infant to encircle the infant's waist and hold diaper 10 on the infant. Rear waist portion 32 and front waist portion 33 each have a width which extends from rear edge 35 and front edge 36, respectively, toward lateral center line 29 a distance of from about 2.5 centimeters (cm) to about 6.4 cm; each has a length which extends transversely across diaper 10 at rear edge 35 and at front edge 36, respectively. The depth of rear and front waist portions, 32 and 33 respectively, is established primarily by and includes the diaper fastening means for affixing the diaper around the waist of the infant. An acceptable fastening means is adhesive fastening tapes 38 as are well known in the disposable diaper art.

Crotch portion 32 of diaper 10 is that area of the diaper which is generally located directly between the legs and around the lower portion of an infant when diaper 10 is worn; it is generally centered on lateral centerline 29.

Absorbent core 14 can be manufactured in a wide variety of sizes and from a wide variety of absorbent materials commonly used in disposable absorbent articles and which are capable of absorbing and retaining liquids. While comminuted wood pulp, generally referred to as airfelt, is preferred for the manufacture of absorbent core 14, other liquid absorbent materials such as foams, a multiplicity of piles of creped cellulose wadding, superabsorbent polymers, or any equivalent material can also be used. The total absorbent capacity of absorbent core 14 should, naturally be compatible with the projected liquid loadings in the intended use of the absorbent article.

The preferred embodiment illustrated in FIG. 1 has an hourglass-shaped absorbent core 14 wherein absorbent core 14 in rear and front waist portion 32 and 33 respectively is wider than is absorbent core 14 in crotch portion 34, thereby forming ears 39, 40, 41, and a fourth ear which is not shown, at the corners of absorbent core 14. The embodiment illustrated in FIG. 1 is intended to be worn by infants ranging in weight from about 5 kilograms (kg) to about 12 kg. Absorbent core 14 is, therefore, a pad of airfelt about 40 cm long when measured along longitudinal centerline 28; it is about 25 cm wide across rear and front waist portions 32 and 33, respectively; and it is about 10 cm wide across crotch portion 34. The absorptive capacity of the airfelt used for absorbent core 14 is sufficient to absorb and retain from about 8 grams (g) to about 16 g of water per gram of absorbent. Accordingly, the airfelt used in the preferred embodiment shown in FIG. 1 weighs from about 30 g to about 56 g. It should understood, however, that the size, shape, and total absorbent capacity of absorbent core 14 can be varied to accommodate diaper users ranging in size from newly born infants through adults. Thus other dimensions, and even other shapes (e.g., rectangular), can also be used for absorbent core 14.

Absorbent core 14 has a core edge 43 which defines the outer extent of the absorbent core 14 and which comprises a multiplicity of core edge segments; a core edge segment is a portion of the core edge 43. Preferably, core edge 43 comprises a front end segment 45 which is the core edge segment traversing the end of absorbent core 14 at front waist portion 33 of diaper 10 and a rear end segment 47 which is the core edge segment traversing the end of absorbent core 14 at rear waist portion 32 of diaper 10. Core edge 43 has a core edge surface 42 (FIG. 2) which faces away from the center of absorbent core 14 in rear waist portion 32. Core edge 43 has a similar core edge surface in front waist portion 33, but that surface is not shown explicitly in the figures.

As seen most clearly in FIG. 2, a preferred absorbent core 14 comprises an absorbent layer 44, and first tissue layer 46 which forms first opposed surface 48 of absorbent core 14, and a second tissue layer 50 which forms a second opposed surface 52 of absorbent core 14. Core edge surface 42 joins first and second opposed surfaces 48 and 52. Thus, the outer surfaces of absorbent core 14 in rear waist portion 32 are defined by first opposed surface 48, second opposed surface 52, and core edge surface 42.

Absorbent layer 44 is preferably comminuted wood pulp, but can be any of the absorbent materials hereinbefore described. First and second tissue layers 46 and 50 enhance the tensile strength of absorbent layer 44 and reduce the tendency of absorbent layer 44 to lose its shape when wetted. While a number of materials and manufacturing techniques can be used to manufacture tissue layers 46 and 50, satisfactory results have been obtained with sheets of wet strength tissue paper having a basis weight of about 16 g per square meter (m). While tissue layers 46 and 50 are preferably coterminous with absorbent layer 44, they can have different dimensions, a different configuration, or they can be omitted entirely.

Second tissue layer 50 of absorbent core 14 is superposed on backsheet 16 and is preferably attached thereto by attachment means (not shown) well known in the art.

Backsheet 16 is impermeable to liquids and prevents the liquids absorbed by absorbent core 14 from wetting the undergarments, clothing, bedding, and other objects which contact the person wearing disposable diaper 10. Preferably, backsheet 16 is a polyethylene film from about 0.0012 mm to about 0.051 mm thick, although other flexible, liquid impermeable materials can also be used. As user herein, the term "flexible" refers to materials which are compliant and which are readily conform to the shape and contours of the human body. A suitable polyethylene film is manufactured by Monsanto Chemical Company of St. Louis, Mo., and marketed in the trade as film No. 8020. Materials used in the art to provide backsheets which are generally liquid impermeable but vapor permeable (i.e. "breathable") can also be used.

In a preferred embodiment, backsheet 16 has a modified hourglass configuration and extends beyond core edge 43 a distance of from about 1.5 cm to about 3.0 cm in rear and front waist portions 32 and 33. Along longitudinal sides 24 of diaper 10, the backsheet 16 extends beyond and is generally parallel to the core edge 43. As absorbent core 14 becomes narrower in crotch portion 34, the edge of backsheet 16 is substantially linear and parallel to longitudinal centerline 28 so that backsheet 16 is wider than absorbent core 14 and side flap 22 becomes increasingly wider until lateral centerline 29 is reached. This linear portion on backsheet 16 forms expansible edge 49 of side flap 22. The linear portion of the lateral edge of backsheet 16 is generally between 12 cm and 30 cm long and, for diaper 10 of the preferred embodiment illustrated in FIG. 1, is about 23 cm long. Backsheet 16 is preferably embossed or matte finished to provide a cloth-like appearance.

Topsheet 12 is compliant, soft feeling, and non-irritating to the wearer's skin. Further, topsheet 12 is fluid permeable thereby permitting liquids to readily penetrate through its thickness. It prevents the wearer of the diaper 10 from contacting absorbent core 14. A suitable topsheet can be manufactured from a wide range of materials such as natural fibers (e.g., wood or cotton fibers), synthetic fibers (e.g., polyester or polypropylene), or a combination thereof. Alternatively, topsheet 12 can be a fiber-like foam such as the reticulated foams which are well known in the art.

A particularly preferred topsheet material comprises staple length polypropylene fibers having a denier of about 1.5, such as Hercules 151 polypropylene fibers marketed by Hercules, Inc. of Wilmington, Del. As used herein, the term "staple length fibers" refers to those fibers having a length of at least 3.8 cm.

Suitable topsheets can also be constructed from apertured plastic films such as those described by Radel and Thompson in U.S. Pat. No. 4,342,314, issued Aug. 3, 1982, Ferguson and Landrigan in U.S. Pat. No. 4,341,217, issued July 27, 1982; and Thompson in U.S. Pat. No. 3,929,135, issued Dec. 30, 1975. These three patents are incorporated herein by reference.

Clearly, there are a number of manufacturing techniques which may be utilized to manufacture topsheet 12. For example, topsheet 12 may be woven, nonwoven, spunbonded, carded, or the like and thermally bonded by means well known to those skilled in the art. Preferably, topsheet 12 has a basis weight from about 18 g to about 25 g per square yard, a minimum dry tensile strength of at least about 400 g per cm in the machine direction and a minimum wet tensile strength of at least about 55 g per cm in the cross-machine direction.

Waistshield/waistband 18 is provided at either or both of front end segment 45 of absorbent core 44 and at rear end segment 47 of absorbent core 14. In the description that follows, reference will be made to waistshield/waistbands 18 in both front waist portion 33 and rear waist portion 32 on disposable diaper 10 although only waistshield/waistband 18 is shown in FIG. 1 in front waist portion 33. While this is a preferred construction, it is possible that waistshield/waistband 18 is present in only one of front waist portion 33 and rear waist portion 32. When only one waistshield/waistband 18 is present in disposable diaper 10, it is preferably in front waist portion 33. Further, as illustrated in FIG. 1, waistshield/waistband 18 extends essentially the full lateral width of absorbent core 14. While this is one preferred configuration, in alternate preferred embodiments, waistshield/waistband 18 can extend across all or across only a smaller portion of the lateral width of diaper 10.

Waistshield/waistband 18 serves two functions: it provides an elastically expansible waistband (which will be discussed more fully hereinafter), and it serves as a barrier member intended to prevent premature leakage of the liquid absorbed by absorbent core 14 from end segments 45 and 47 of diaper 10.

The hereinbefore mentioned European Patent Application No. 82200161.6, incorporated herein by reference, describes barrier members along other portions of disposable diaper 10, such as along other portions of core edge 43. Such optical barrier members are not illustrated in the figures.

Waistshield/waistband 18 provides front waistband 78 in front waist portion 33 and rear waistband 70 in rear waist portion 32.

Waistband/waistshield 18 can preferably be formed from polymeric materials which contract unidirectionally and become elastic following specific treatment such as heating. Elastic materials are known which can be heated to their transition temperature and stretched into an elongated orientation. They are then cooled and become relatively inelastic and fixed in their new elongated orientation. Subsequent heating causes the materials to contract to their initial (unstretched or relaxed) orientation and to regain their elasticity. Examples of such materials are shown in U.S. Pat. No. 3,819,401, issued June 25, 1974 to Massengale et al and U.S. Pat. No. 3,912,565, issued Oct. 14, 1974 to Koch et al, both incorporated herein by reference. When such materials are used as waistband/waistshield 18, the topsheet, backsheet, and the waistband/waistshield are preferably affixed together by transverse regions of securement while all three are in their nonelastic orientations. The system is then heated (as with heated air) and the polymeric material is allowed to return to its relaxed (or contracted) and elastic orientation. (As discussed hereinafter, only the waistband portion of the waistband/waistshield 18 is heated and allowed to revert to its contracted and elastic state.) Because waistshield/waistband 18 also functions as a moisture barrier, the material from which it is constructed must be liquid impermeable.

An examination of FIG. 2 reveals waistband/waistshield 18 compries inward portion 56 and outward 57. Inward portion 56 provides the waistshield aspect of waistband/waistshield 18 while outward portion 57 provides the waistband aspect. For convenience, the two aspects will be discussed separately.

Inward position 56 is interposed between topsheet 12 and absorbent core 14 and extends from core edge surface 42 generally toward the center of absorbent core 14 a distance sufficient to provide protection against leakage of liquid from the portion of first opposed surface 48 in proximity to core edge surface 42. It has been found that extending inward portion 56 a distance of from about 0.6 cm to about 9 cm from core edge surface 42 generally toward the center of absorbent core 14 is sufficient to provide protection against liquid leakage. Inward portion 56 can be affixed to either or both of topsheet 12 and absorbent core 14 by means known to the art.

Topsheet 12 has liquid migration resistant segments 58 corresponding to each inward portion 56 of waistband/waistshield 18. Liquid migration resistant segments 58 comprise a compacted portion 60 which alters the flow pattern of liquid as it moves from the point of discharge toward core edge 43 of absorbent core 14. The desired affect of compacted portion 60 may be achieved in many ways such as by filling the interstitial voids of the compacted portion 60 with an adhesive or other liquid impermeable material. In this manner, compacted portion 60 is made to act as a barrier to movement of liquid. In a preferred embodiment, however, compacted portion 60 is compressed or densified relative to the other portions of topsheet 12, which uncompacted portions for convenience are designated portions 64 (FIG. 2). In other words, both the spacing between fibers and the interstitial void volume are reduced in compacted portion 60 to an extent sufficient to cause compacted portion 60 to exhibit a greater capillary attraction for liquid than uncompacted portion 64. Thus, liquid contacting compacted portion 60 will wick into and through the compacted portion 60. Compacted portion 60, therefore, alters the liquid flow pattern and by configuring compacted portion 60 liquid is redirected away from those parts of the diaper from which leakage may occur.

The ratio of the caliper of uncompacted portion 64 of topsheet 12 to the caliper of compacted portion 64 of topsheet 12 to the caliper of compacted portion 60 is at least about 1.5:1 and preferably at least about 2.0:1. Most preferably, the ratio of the caliper of uncompacted portion 64 to the caliper of compacted portion 60 is at least 4:1. It should be understood the term "caliper" refers to thickness only and does not in any way refer to the relative elevations of compacted and uncompacted portions 60 and 64. Therefore, compacted portion 60 may have a higher elevation that uncompacted portion 64, or, as shown in FIG. 2, compacted portion 60 may be depressed below the surface of uncompacted portion 64.

Many procedures are suitable for determining the ratio of the caliper of uncompacted portion 64 to the caliper of compacted portion 60. For example, a simple optical procedure may be used whereby a strip of the topsheet is cut perpendicular to compacted portion 60. By viewing the edge of the strip through a microscope having a calibrated eyepiece, the calipers of uncompacted portion 64 and of compacted portion 60 can be determined. From the individual calipers, the ratio of the calipers is easily calculated.

Compacted portion 60 of topsheet 12 is affixed to waistband/waistshield 18 using any suitable means which will provide a liquid retarding bond between topsheet 12 and waistband/waistshield 18. Thus, liquid migration along the interfacial junction between topsheet 12 waistband/waistshield 18 is retarded and is preferably prevented. In a preferred embodiment, heat sealing along compacted portion 60 as is well known in the art is satisfactory. The use of heat sealing techniques to affix compacted portion 60 to has the additional advantage of compressing compacted portion 60 at the same time it is affixed to waistband/waistshield 18.

Compacted portion 60 corresponds to each waistband/waistshield 18 and is intended to retard liquid which flows along the surface of topsheet 12, liquid which is absorbed by topsheet 12, and liquid which flows in the capillary channel formed between topsheet 12 and the skin of the wearer, from wetting the vicinity surrounding diaper 10. Accordingly, compacted portion 60 is configured so as to render the path followed by the above identified liquids tortuous and preferably impassible. Thus, each compacted portion 60 preferably comprises a multiplicity of continuous bands 61 defining reservoirs 62 therebetween. Reservoirs 62 are preferably neither compacted nor affixed to waistband/waistshield 18.

In the embodiment illustrated in FIGS. 1 and 2, compacted portion 60 comprising a multiplicity of continuous bands 61 is provided in both the front waist portion 33 and rear waist portion 32 corresponding to each waistband/waistshield 18. Bands 61 are shown for purposes of simplicity as straight lines which are generally parallel to edges 35 and 36 and which preferably traverse the entire lateral length of waistshield/waistband 18. Undulating lines extending across essentially the same region are also effective and are, in some cases, preferred.

The combination of bands 61 and reservoirs 62 promote a redirection and absorption of liquids so that the liquids will not reach a point from which they can wet the vicinity surrounding diaper 10. Bands 61 have a width of at least 0.25 mm and preferably at least about 1.6 mm while reservoirs 62 have a width of at least about 0.9 mm and preferably at about least 2.3 mm. The narrower the width of bands 61 and reservoirs 62, the more readily liquid will bridge them without being redirected or absorbed.

Waistband/waistshields 18 are affixed to both topsheet 12 and backsheet 16 in front waistband 78 and rear waistband 70. While any of numerous well known means of attachment can be used (e.g. adhesive attachment, ultrasonic welding, etc.), the three elements are preferably joined by transverse regions of securement 75.

Figure 3:
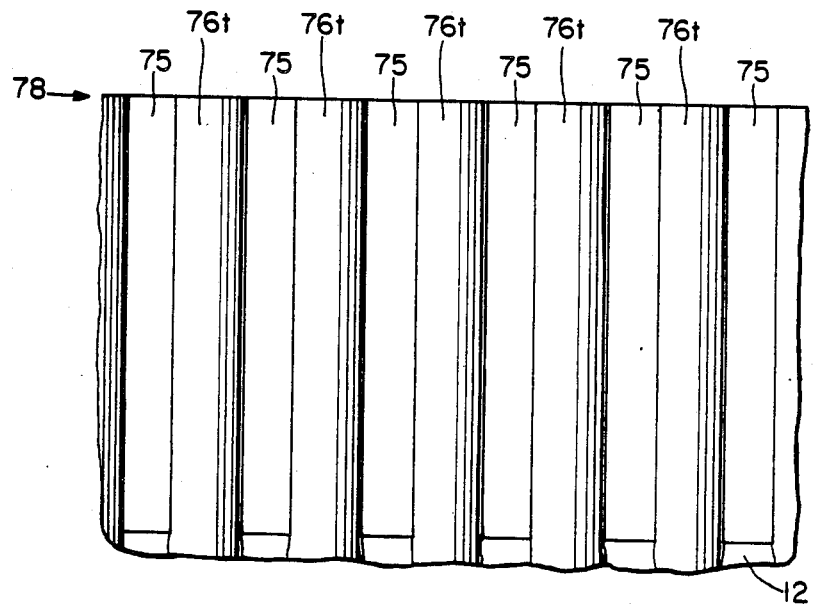
FIG. 3 is an enlarged partial view of the waistband of the diaper of FIG. 1 illustrating an embodiment of the diaper waistband.
Figure 4:
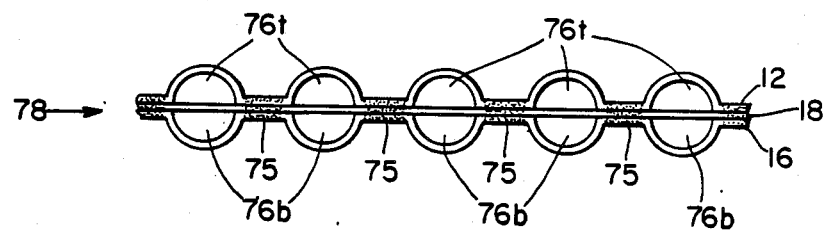
FIG. 4 is an end view of the portion of the waistband shown in FIG. 3.

Transverse regions of securement 75 are shown in a generalized representation in FIG. 1.A a more specific embodiment of transverse regions of securement 75 is depicted in FIGS. 3 and 4 which are enlarged views of a portion of front waistband 78 indicated by reference numeral 3 in FIG. 1.

It must be noted that FIGS. 3 and 4 illustrate diaper 10 after waistband/waistshield 18 has been contracted as with heat air as described; infra; FIGS. 1 and 2 illustrate diaper 10 before such contraction.

In this discussion of FIGS. 3 and 4, reference shall be made to front waistband 78 and the components thereof. The same comments can be made about rear waistband 70 and its components since the two waistbands can each benefit from use of the present invention.

Transverse regions of securement 75 extend essentially across the whole of the distance over which waistband/waistshield 18, topsheet 12, and backsheet 16 are in contact.

The term "transverse" as used in the context refers to an orientation generally perpendicular to the major laterally extending dimension of waistband 78. That is to say, since front waistband 78 extends laterally across the width of disposable diaper 10 and is generally parallel to lateral center line 29, transverse regions of securement 75 extend across front waistband 78 in an orientation essentially parallel to longitudinal center line 28; they are directed generally from front edge 36 toward the center of disposable diaper 10. As illustrated, transverse regions of securement 75 are shown to be at essentially right angles to lateral center line 29 and to the lateral extend front waistband 78. This is the preferred orientation. They can, however, depart from true transversity. The departure from true (or absolute) transversity becomes too great when channels (as hereinafter discussed) are no longer formed extending essentially across the width of front waistband 78. In general, departure from transversity becomes too great for practical operation when the departure from transversity exceeds about 45° from perpendicularity to lateral center line 29.

The term "essentially across" is used in this context to indicate that transverse regions of securement 75 need not extend absolutely across the entire width of waistband so long as they extend sufficiently far across the width thereof to provide the channels discussed hereinafter.

In FIG. 3, transverse regions of securement 75 are shown as essentially regularly spaced unitary zones of sealing attaching waistband/waistshield 18 to topsheet 12 and backsheet 16 which is not visible in FIG. 3. The precise means for providing the zones of sealing can be readily selected by those skilled in the art. Examples include adhesive attachment, heat sealing, solvent sealing and the like. Preferably, ultrasonic welding is used.

As illustrated in FIGS. 3 and 4, the points of attachment of both topsheet 12 and backsheet 6 to waistband/waistshield 18 are in register (i.e., are coextensive).

This is a preferred orientation, but the points of attachment of topsheet 12 to waistband/waistshield 18 can be offset from the adjacent points of attachment of backsheet 16 to waistband/waistshield 18. In such a situation there will be offset transverse regions of securement on either side of the elastic waist element.

In an alternate embodiment, the transverse regions of securement can comprise discrete spaced zones of sealing, preferably ultrasonic welds, effectively attaching the materials together and forming the channels hereinafter described. Preferably, in this alternate embodiment, the discrete spaced zones are essentially rectangular.

Transverse regions of securement 75 can be from about 0.15 cm to about 1.0 cm wide (i.e., in the dimension generally parallel to lateral centerline 29. They are preferably regularly spaced, but they can be nonuniformily spaced. They are preferably from about 0.3 cm to about 1.5 cm apart as measured from center to center.

FIG. 4 illustrates the functioning of the regions of securement. FIG. 4 is an end view of the portions of front waistband 10 shown in FIG. 3 with waistband/waistshield 18 in a contracted position. In FIG. 4, transverse regions of securement 75 are shown in darkened portions for emphasis. Since waistband/waistshield 18 is in its relaxed or contracted position, topsheet 12 and backsheet 16 are shown gathered. These gathers constitute and define transverse regions of nonsecurement $76b$ between backsheet 16 and waistband/waistshield 18 and transverse regions of nonsecurement $26t$ between topsheet 12 and waistband/waistshield 18. These transverse regions of nonsecurement $76b$ and $76t$ form open gathers or channels from the margin of the diaper extending to the interior of the diaper and terminating in the region adjacent the core edge surface 42. These open channels allow the diaper to breathe by allowing the exchange of air and vapor between the interior of the diaper and the surrounding atmosphere even when the diaper is secured about an infant.

At the same time as transverse regions of nonsecurement $76b$ and $76t$ are formed, topsheet 12 and backsheet 16 form structures in the nature of corrugations. These corrugations extend transversely across the width of rear waistband 70 tend to stiffen the waistband thereby tending to prevent waistband rollover (i.e., the bending of the waistband about itself.) Further, the elastic nature of the material in waistshield/waistband 18 allows the diaper to be fastened about the waist of the user and in close relation to the user's body thereby providing better fit and reducing leakage of liquids from the diaper at the user's waist.

In the final form of diaper 10, (i.e., diaper 10 as it is ready for use), at least one of rear waistband 70 and front waistband 78, preferably both, must be elastically expansible. That is to say, at least one of the waistbands must be relatively stable, normally gathered, at the time diaper 10 is ready to be placed about the wearer's waist, it must be capable of elongation ("stretching") as it is fitted about the wearer's waist, and it must remain elastically expansible to form a relatively snug, but yielding fit about the wearer's waist. (In extremely simple terms, the diaper must have an elastic waist.)

As before, the following discussion will be directed only to rear waistband 70 of diaper 10; similar comments can be made regarding front waistband 78.

Waistshield/waistband 18 is the element which imparts the noted qualities to diaper 10. Since waistshield/waistband 18 is a unitary structure, outward portion 57 must have different properties than inward portion 56 in diaper 10 as the latter is ready for use. At the time of use, outward portion 57 must be effectively more elastic that inward portion 56; outward portion 57 preferably is shorter in the lateral direction than inward portion 56 so that waistband 70 can be readily elongated independently of core surface edge 42 of core 14. In use, outward portion 57 will preferably extend to from about 105% to about 150% of its original length under an applied elongation force of 100 gm per cm. These objects can be accomplished if waistshield/waistband 18 is constructed of the aforementioned material which has a heat unstable state and a heat stable and elastic state.

Waistshield/waistband 18 is incorporate in diaper 10 while the material is in its heat unstable state. It is then differentially heated so as to cause outer portion 57 to revert more fully to its heat stable and elastic state than inward portion 56. Restriction of heating to outer portion 57 can be accomplished in any convenient fashion. For example, hot air nozzles can be constructed so as to direct heated air primarily to the region of outer portion 57 while excluding any significant flow of heated air to inner portion 56. During the course of this reversion, waistband 70 is gathered since outward portion 57 is affixed therein, and waistband 70 becomes elastic relative to diaper 10 at core edge surface 42.

In preferred embodiments, the waistband portion contracts from about 5% to about 50%, preferably from about 10% to about 30%. The waistband portion contracts no more than about 10%, preferably no more than about 5%. (Percent contraction is defined as 100 times the quotient obtained when the difference between the uncontracted length of the element and its contracted length is divided by its uncontracted length).

In a simple method of differential heating, diaper 10 is folded so that the lateral margins of waist portions 32 and 33 are lapped one over another, as by folding diaper 10 into three essentially equal portions along two longitudinally extending axes. Diaper 10 can also optionally and conveniently be folded upon itself along lateral center line at 29 by bringing front waist portion 33 into proximity with rear waist portion 32. (It will be observed that the general configuration described is that which diaper 10 would have as it is prepared for packaging.) Hot air is then directed at the waist portions of diaper 10 for a time that can be easily determined for any temperature and rate of flow of air. Outer portion 57 of waistshield/waistband 18 is quickly heated and converted to its heat stable and elastic state (i.e. it is "heat shrunk"). Inner portion 56 of waistshield/waistband 18, on the other hand, is insulated from the hot air by absorbent core 14 and the other diaper components; it either reverts not at all or only slighty toward its heat stable and elastic state. Thus the desired characteristics are imparted to diaper 10.

From the above discussion it should be apparent that some degree of reversion toward the heat stable elastic state of inward portion 56, and hence gathering and imparting of elasticity to absorbent core 14 at core edge surface 42 is acceptable. The gathering of absorbent core 14 at core edge surface 42 should be only slight compared to the gathering of rear waistband 70, however.

As an alternate, but less preferred, construction, waistshield/waistband 18 can be constructed of any conventional elastic material. In its relaxed (unextended) state, outer portion 57 of waistshield/waistband 18 will be shorter in the lateral direction than inner portion 56. That is to say, in plan view, when in the relaxed state, waistshield/waistband 18 constructed of conventional elastic material, is not a rectangle. Inner portion 56 is affixed to topsheet 12, as described above, in its relaxed state. Outward portion 57 is then elongated and contractibly affixed to topsheet 12 and backsheet 16, as described above, in its elongated state. When the elongating forces are released, outer portion 57 will tend to return toward its relaxed configuration thereby gathering waistband 70 and rendering it elastic as required while inward portion 56 maintains nearly its original configuration. Differential elasticity between the two portions is created by absorbent core 14 which will resist elongation to some extent.

EXAMPLE

A disposable diaper is made according to the teachings of this invention. It is constructed as illustrated in FIGS. 1 and 2. It is constructed so as to have a unitary waistshield and elastically expansible waistband in the front margin thereof and an elastically expansible waistband in the rear margin. The tophseet is formed of carded polypropylene fiber having a basis weight of about 24 gm per square m as supplied by Scott Paper Company of Philadelphia, Pa. The topsheet has the plan form illustrated in FIG. 1; it is about 45 cm in longitudinal length and about 32 cm wide at each end. The backsheet is 0.03 mm thick polyethylene film as supplied by Monsanto Company of St. Lous, Mo. It is essentially the same plan form and size as the tophsheet. The absorbent core is formed of airlaid wood pulp fibers made by The Buckeye Cellulose Corporation of Memphis, Tenn. The absorbent core is approximately 25 cm wide at each end and approximately 10 cm wide in the crotch region. It is approximately 40 cm long in the longitudinal dimension. The airfelt core weighs approximately 54 gms. A rectangular sheet of tissue paper approximately 39 cm long and 11 cm wide, having a basis weight of about 18 gm per square m, is placed on each side of the airfelt core. Thirty longitudinally extending bands of hotmelt adhesive as made by Eastman Chemical Company of Kingsport, Tenn., secure the absorbent core to the backsheet. The topsheet is affixed to the backsheet in the side flaps with this hotmelt adhesive. The diaper is supplied with 2 fastening tapes affixed to the rear waistband. An elastomeric film having a heat unstable state and a heat stable and elastic state, as manufactured by Exxon Chemical Company of Houston, Texas, which is tentered in its cross machine direction so as to provide a recovering force after heating to 140° F. for 30 minutes of from about 160 to about 400 gm per cm at 100% elongation is used in the rear waist portion of the diaper and in the front waist portion of the diaper. In the rear waist portion, the material is about 22 cm long and about 2.5 cm wide; it functions, after being subjected to heat, as an elastically expansible waistband. The polymeric film in the front waist portion is about 22 cm long and about 5 cm wide; it functions as the unitary waistshield and elastically expansible waistband of the present invention. After assembly, the rear waistband of the diaper is heated to provide about 30% contraction while the front waist region of the diaper is differentially heated to provide about 30% contraction of the elastomeric material in the waistband portion and less than about 10% contraction in the waistband portion.

The disposable diaper, when used on an infant, functions properly for its intended purpose.

What is claimed is:

1. A disposable diaper having at least one elastically expansible waistband extending across at least a portion of at least one lateral edge of said diaper, said diaper comprising:
   (a) A fluid permeable topsheet;
   (b) A liquid impermeable backsheet;
   (c) An absorbent core interposed between said topsheet and said backsheet; and
   (d) At least one unitary waistshield and elastically expansible waistband member having an inward portion and an outward portion, said member extending along at least a portion of said at least one lateral edge of said diaper, said inward portion of said member interposed between said topsheet and said absorbent core, said outward portion of said member interposed between said topsheet and said backsheet and being affixed thereto,
wherein said at least one elastically expansible waistband comprises said outward portion of said unitary waistshield and elastically expansible waistband member.

2. The disposable diaper of claim 1 wherein said outer portion is affixed to said topsheet and to said backsheet by essentially regular transverse regions of securement defining therebetween transverse regions of nonsecurement extending from the outer margin of said elastically expansible waistband across essentially the entire width of said waistband.

3. The diaper of claim 2 wherein said transverse regions of securement comprise zones of sealing comprising ultrasonic welds.

4. The diaper of claims 1, 2, or 3 wherein said unitary waistshield and elastically expansible waistband member comprises an elongate elastomeric material having a heat unstable state and a heat stable and elastic state; said outward portion being relatively more heat stable and elastic than said inward portion.

5. The diaper of claim 4 wherein said topsheet comprises a multiplicity of liquid migration resistant segments corresponding to said inward portions of said unitary waistshield and expansible waistband member, said liquid migration resistant segments having compacted portions affixed to said inward portion.

6. The diaper of claim 1, 2 or 3 wherein said topsheet comprises a multiplicity of liquid migration resistant segments corresponding to said inward portion of said unitary waistshield and expansible waistband member, said liquid migration resistant segments having compacted portions affixed to said inward portion.

* * * * *

UNITED STATES PATENT AND TRADEMARK OFFICE
CERTIFICATE OF CORRECTION

PATENT NO. : 4,681,580

DATED : July 21, 1987

INVENTOR(S) : George S. Reising & Jerry L. Dragoo

It is certified that error appears in the above-identified patent and that said Letters Patent is hereby corrected as shown below:

Column 2, line 50 "waistband" should read --waistshield--;
Column 2, line 53, "form" should read --from--.
Column 4, line 12, "32" should read --34--;
Column 4, line 48, "should understood" should read --should be understood--.
Column 5, line 2, "and first" should read --and a first--;
Column 5, line 37, "which are readily" should read --which readily--.
Column 8, line 9, "that" should read --than--;
Column 8, line 33, "60 to has" should read --60 has--;
Column 8, line 67, "at about least" should read --at least about--.
Column 9, line 30, "the context" should read --this context--.
Column 11, line 16, "incorporate" should read --incorporated--.
Column 12, line 32, "Lous" should read --Louis--;
Column 12, line 33, "tophsheet" should read --topsheet--;
Column 12, line 68, "waistband" should read --waistshield--.

Signed and Sealed this

Twenty-ninth Day of December, 1987

Attest:

DONALD J. QUIGG

Attesting Officer

Commissioner of Patents and Trademarks